US006916308B2

(12) United States Patent
Dixon et al.

(10) Patent No.: US 6,916,308 B2
(45) Date of Patent: Jul. 12, 2005

(54) HIGH PRESSURE INJECTION SYRINGE

(75) Inventors: Christopher G. Dixon, Bloomington, IN (US); Jacob A. Flagle, Indianapolis, IN (US); Andrew K. Hoffa, Bloomington, IN (US); Joseph P. Lane, Methuen, MA (US)

(73) Assignee: Cook Incorporated, Bloomington, IN (US)

( * ) Notice: Subject to any disclaimer, the term of this patent is extended or adjusted under 35 U.S.C. 154(b) by 353 days.

(21) Appl. No.: 09/875,532

(22) Filed: Jun. 6, 2001

(65) Prior Publication Data

US 2002/0010431 A1 Jan. 24, 2002

Related U.S. Application Data

(60) Provisional application No. 60/210,316, filed on Jun. 8, 2000.

(51) Int. Cl.[7] .................................................. A61M 1/00
(52) U.S. Cl. ....................................................... 604/122
(58) Field of Search .......................... 604/122, 128–129, 604/181, 187, 208–211, 231

(56) References Cited

U.S. PATENT DOCUMENTS

| 2,283,915 A | 5/1942 | Cole |
| 2,475,939 A | 7/1949 | Applezweig |
| 3,417,971 A | 2/1967 | Blank et al. |
| 3,353,718 A | 11/1967 | McLay |

(Continued)

FOREIGN PATENT DOCUMENTS

| DE | 2814353 | 10/1978 |
| DE | 2801706 | 7/1979 |
| WO | 9949819 | 10/1999 |
| WO | WO 9965597 | 12/1999 |

OTHER PUBLICATIONS

Percutaneous Vertebroplasty: State of the Art; A. Cotten, N. Boutry, B. Cortet, R. Assaker, X. Demondion, D. LeBlond, P. Chastanet, B. Duquesnoy, & H. Deramond; RadioGraphics; vol. 18, No. 2; Mar.–Apr. 1998; pp. 311–323.
Controlled Delivery for Oseteoplasty; A Vertebroplasty Application; American OsteoMedix; Technique Manual.

*Primary Examiner*—LoAn H. Thanh
(74) *Attorney, Agent, or Firm*—Brinks Hofer Gilson & Lione

(57) ABSTRACT

A pressure injection syringe (10) with an actuator (100) that includes a plunger (102) for pressurizing viscous fluid material within a chamber (14). The plunger distal tip (112) includes a high pressure seal (110) defined by a seal member (118) within a seal seat (116). The high pressure seal (110) is viscoselective to permit air passage therepast for aspiration, and to prohibit viscous material passage therepast during actuation of the actuator wherein high pressure is applied to the material within the chamber (14). The viscoselective seal (110) may be defined for example by small axial openings (130) in the seal seat (116) that permit aspiration of air therepast during initial plunger insertion into the chamber, but fluid escape is prohibited by the seal member (118) when the seal member is pressed firmly against a collar (126) of the plunger (102) proximally adjacent the seal seat by initial engagement of the seal member with the viscous material, thus completely sealing the chamber (14) at the proximal end thereof.

12 Claims, 6 Drawing Sheets

U.S. PATENT DOCUMENTS

| | | | |
|---|---|---|---|
| 3,750,667 A | | 8/1973 | Pshenichny et al. |
| 4,013,080 A | | 3/1977 | Froning |
| 4,189,065 A | | 2/1980 | Herold |
| 4,277,184 A | | 7/1981 | Solomon |
| 4,312,343 A | | 1/1982 | LeVeen et al. |
| 4,346,708 A | | 8/1982 | LeVeen et al. |
| 4,367,739 A | | 1/1983 | LeVeen et al. |
| 4,583,974 A | | 4/1986 | Kokernak |
| 4,632,672 A | * | 12/1986 | Kvitrud ...................... 604/222 |
| 4,655,749 A | | 4/1987 | Fischione |
| 4,671,263 A | | 6/1987 | Draenert |
| 4,710,179 A | * | 12/1987 | Haber et al. ................. 604/211 |
| 4,793,363 A | | 12/1988 | Ausherman et al. |
| 4,810,249 A | | 3/1989 | Haber et al. |
| 4,832,692 A | * | 5/1989 | Box et al. ................ 604/99.01 |
| 4,865,591 A | * | 9/1989 | Sams ......................... 604/186 |
| 4,966,601 A | | 10/1990 | Draenert |
| 4,969,888 A | | 11/1990 | Scholten et al. |
| 5,015,101 A | | 5/1991 | Draenert |
| 5,108,404 A | | 4/1992 | Scholten et al. |
| 5,213,115 A | | 5/1993 | Zytkovicz et al. |
| 5,290,260 A | | 3/1994 | Stines |
| 5,306,248 A | | 4/1994 | Barrington |
| 5,618,273 A | | 4/1997 | Fischer |
| 5,653,730 A | | 8/1997 | Hammerslag |
| 5,759,194 A | | 6/1998 | Hammerslag |
| 5,843,124 A | | 12/1998 | Hammerslag |
| 5,865,803 A | * | 2/1999 | Major ...................... 604/122 |
| 6,048,336 A | | 4/2000 | Gabriel |
| 6,050,977 A | | 4/2000 | Adams |
| 6,074,373 A | | 6/2000 | Sudo et al. |
| 6,224,568 B1 | | 5/2001 | Morimoto et al. |

* cited by examiner

HIGH PRESSURE INJECTION SYRINGE

RELATED APPLICATION INFORMATION

This application claims priority from U.S. Provisional Application Ser. No. 60/210,316 filed Jun. 8, 2000.

TECHNICAL FIELD

This relates to the field of medical devices and more particularly to injection syringes.

BACKGROUND OF THE INVENTION

In certain procedures, especially in certain medical procedures, injection syringes are utilized manually to express rather viscous fluids wherein the syringe assemblies must gain substantial mechanical advantage. Particularly in percutaneous vertebroplasty, bone implant material must be injected into a patient's vertebra for stabilization of the spine in osteoporosis and metastatic disease. The biocompatible implant material is viscous, and one such material is polymethylmethacrylate (PMMA). During the procedure, the hard cortical bone of the vertebra is penetrated by a needle such as a standard 11 gauge bone biopsy needle having a cannula and stylet, and then the stylet is removed; a syringe loaded with the bone cement is connected to the proximal end of the relatively narrow cannula; and the plunger is then actuated to express the cement through the cannula and out its distal end and into the intra-vertebral site. Preferably, a syringe containing 10 cc or more volume is utilized, since about 5 to 8 cc of implant material is required per implantation procedure.

In PCT Patent Publication WO 99/49819 is disclosed a high pressure applicator particularly useful in percutaneous vertebroplasty, said to permit the manual generation of about 1000 to 2000 psi of pressure or more, enabling the implant material to be more viscous than prior art syringes allowed which is preferred for the material to remain in place once applied in situ. The large storage capacity of the chamber of the device enables a complete implantation procedure to be performed expeditiously without reloading the device, and the applicator is said to be consistently controllable for an even, constant application of pressure during material delivery. A first column is open ended and defines a chamber for initial receipt of the implant material, and has exterior threads to cooperate with internal threads of a larger diameter second column extending from a rotatable actuator handle. A pressure seal such as an O-ring is provided at the distal end of the second column to seal with the outside surface of the first column for providing a high pressure seal to maintain the air between the first and second columns to enable generation of pressure therebetween during an application procedure. The distal end of the first column has attached thereto a Luer-lock connector to define a connection either to the cannula or to a flexible tube that is connected to the cannula, and a radially extending stabilizer is provided near the distal end of the first column for enabling the operator to grasp and steady the device as the actuator handle at the proximal end of the second column is rotated to generate pressure to the implant material within the chamber.

A similar product sold by Parallax Medical, Inc. of Mountain View, Calif., includes a plunger extending from the second column to move coaxially within the chamber of the first column to apply pressure to the implant material, and includes at the plunger's distal end an O-ring seal in a grooved seat forwardly of a ledge, to engage and compress against the chamber's inner surface as the plunger is moved further into the chamber to prevent implant material from passing therepast during an application procedure. The first column also includes an enlarged threaded open proximal end section, and a complementary second column, enabling better mechanical advantage and also permitting intentional overfill of the chamber proper to remove as much air as possible from the chamber proper once filled with implant material.

Another application device for applying bone cement (as well as mixing the two-part cement) is disclosed in U.S. Pat. No. 4,671,263, wherein a plunger distal end includes a pair of lamellae of flexible material that abut the inside surface of the casing or chamber, and are said to abut tightly enough such that as the plunger is moved distally the lamellae permit air to escape while preventing bone cement from passing. Pressures provided by the syringe are low and said to range from 2 bar to 20 bar (200 kPa to 2 Mpa; or 29.1 to 291 psi).

It is desired to provide a high pressure injection syringe that provides a seal at the proximal end of the chamber that assuredly inhibits passage therepast of viscous material, under pressures of at least 1000 psi (69 bar or 690 Mpa).

It is also desired to provide a high pressure injection syringe that not only provides for a seal under high pressure but also simplifies the air aspiration procedure and also reduces the length of time necessary for the application of the viscous material to the intended site.

It is further desired to provide a high pressure injection syringe that is adapted to manually and controllably generate higher pressures, which in turn permits increasing the viscosity of implant material for enhancing the effectiveness of medical procedures such as vertebroplasty.

SUMMARY OF THE INVENTION

The foregoing and other problems are solved by the high pressure injection syringe of the present invention. The syringe includes a chamber with a distal end such as a tip adapted to be connected to a cannula or flexible tube; an actuator comprising a plunger and an actuation section such as a manually actuatable handle; and a connector to be fixed relative to the chamber for facilitating entry of the plunger into the chamber. The connector preferably includes an advancement mechanism that is adapted to be moved between first and second positions to engage with and disengage from the actuator for providing for both incremental advancement of the plunger in the chamber, and free axial movement thereof, respectively. The plunger distal portion is adapted to define a viscoselective high pressure seal, that is, one which is effective against viscous fluid but does not act as a seal against non-viscous fluids such as air.

In one embodiment, the plunger distal tip portion comprises a circumferential seal seat just proximally of the tip in which is disposed a seal member such as an O-ring so sized for its radially outwardly directed surface to assuredly sealingly engage the inside surface of the chamber during an application procedure but be movable therealong during actuation of the plunger. The seal seat can have a geometry to provide for escape of air between the seal member and the groove bottom surface, and preferably to permit slight axial movement of the seal member within the seal seat. For example, small channels or vents may extend longitudinally from distally of the seal member to proximally thereof prior to the seal member being urged to its most proximal position by the viscous material; the seal member can be an O-ring that can be fabricated of material having a limited resilience, such as polytetrafluoroethylene (PTFE). The seal seat can alternatively be knurled in effect to provide a pattern of grooves defining the vents for air escape. Also, the seat can alternatively be provided with axially extending ribs that are engaged by the O-ring's inwardly directed surface, with the arcuate gap regions between the ribs effectively defining vents.

In another embodiment, one or more very small apertures can be defined extending longitudinally within the plunger tip from distally of the seal member to a location proximally thereof, passing under the seal member or extending internally within the plunger under the seal seat.

In yet another embodiment, the seal member itself can have a geometry, such as grooves on its surface or apertures extending therethrough, that when not under high compression define vents for air passage for aspiration of the chamber, but that close under even slight compression to prevent viscous material passage at the initiation of actuation.

In one aspect of the invention, the connector can have an advancement mechanism that has threaded surfaces to cooperate with corresponding threaded surfaces on the plunger when engaged, so that the plunger is constrained to move longitudinally only incrementally with respect to the connector and the chamber as the handle is rotated. The connector can allow for the advancement mechanism to be moved rotatably, for example, between the first and second positions where in the first position the threaded surfaces have been deflected radially inwardly by a cam of the connector to engage the plunger threads, and where in the second position the threaded surfaces have disengaged from the cam and thus have been permitted to relax or resile radially outwardly to be spaced outwardly from engagement with the plunger allowing the plunger to be moved freely longitudinally with respect to the connector and the chamber.

BRIEF DESCRIPTION OF THE DRAWINGS

An embodiment of the present invention will now be described by way of example with reference to the accompanying drawings, in which.

DETAILED DESCRIPTION

Figure 1:
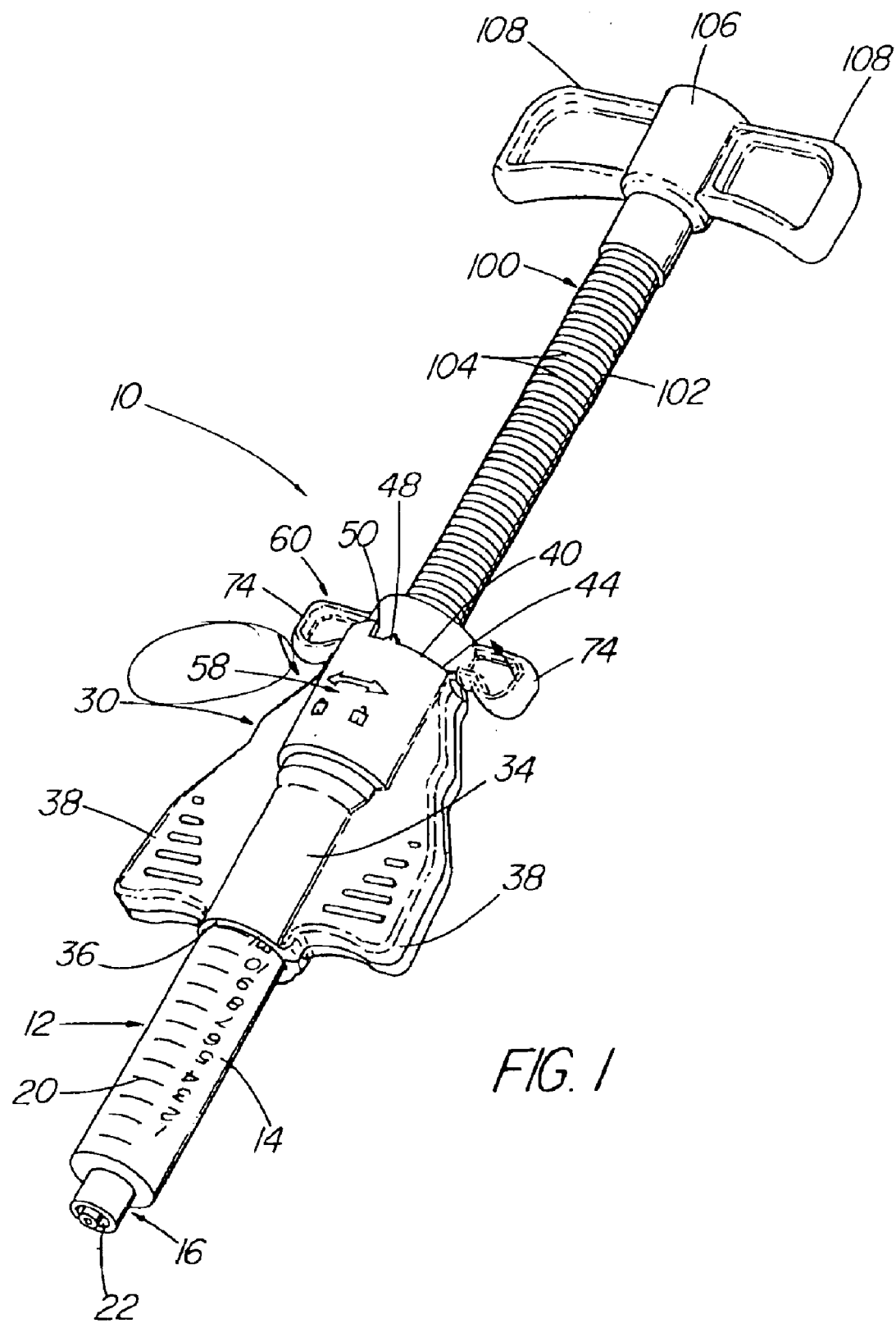
FIG. 1 is an isometric view of the high pressure injection syringe of the present invention.
Figure 2:
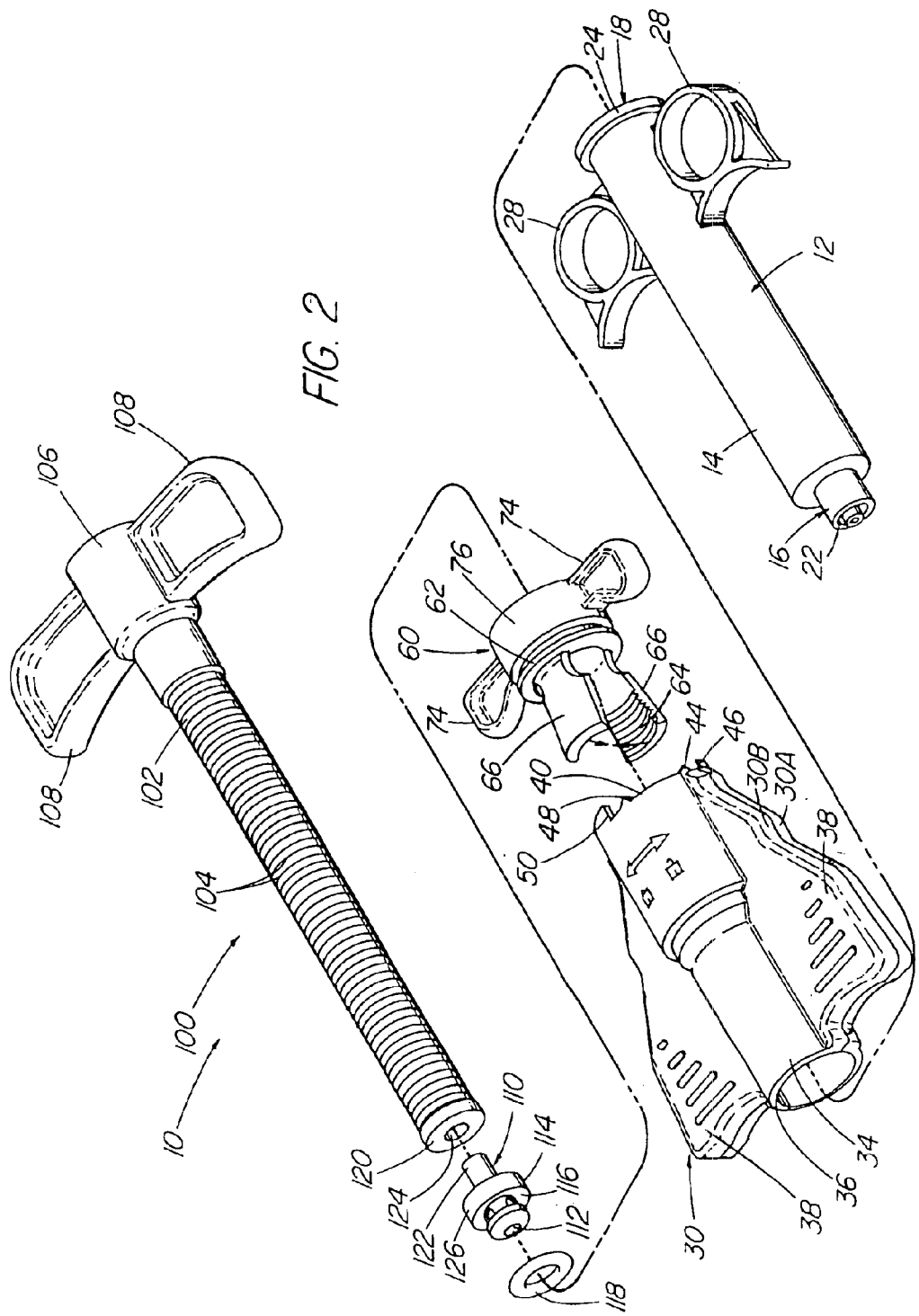
FIG. 2 is an exploded isometric view of the syringe of FIG. 1.

FIGS. 1 and 2 illustrate the high pressure injection syringe 10 of the present invention. A container member 12 includes a chamber 14 that is sufficiently large to provide for an ample quantity of viscous fluid material, and has a distal end 16 and a proximal end 18. Preferably, the chamber 14 includes graduating indicia 20 beginning at distal end 16 and extending toward proximal end 18 for volume measurement of the viscous material. Also, preferably, at least chamber 14 is formed of transparent material to enable visual verification of the volume of viscous material and also the location of the plunger tip and its seal. Distal end 16 is adapted to connect with another apparatus of smaller diameter such as a cannula or flexible tube (not shown) by means of a conventional Luer-lock fitting 22, for expression of the viscous material during an application procedure. A flange or lip 24 is defined at proximal end 26 for facilitating being affixed to a connector 30 having a corresponding flange or lip 32 within a cylindrical body portion 34 as chamber 14 extends beyond distal end 36 of body portion 34. Such a container member, with "finger grips" as shown, is a control syringe available from Merit Medical Systems, Inc. of South Jordan, Utah and is made from polycarbonate plastic.

Figure 3:
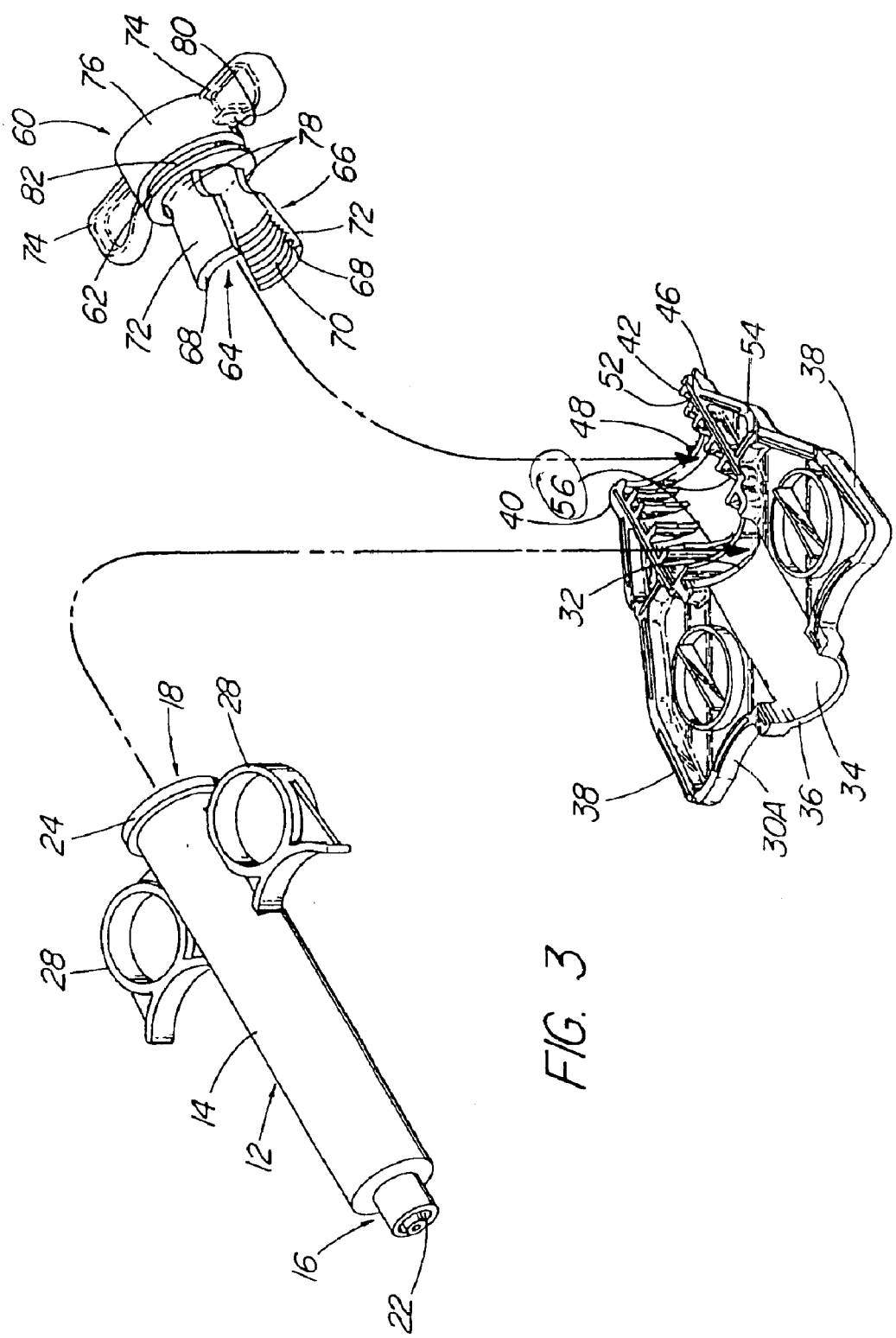
FIG. 3 is an exploded isometric view of one half of the connector, and of the advancement mechanism and the container of the syringe of FIGS. 1 and 2.
Figure 4:
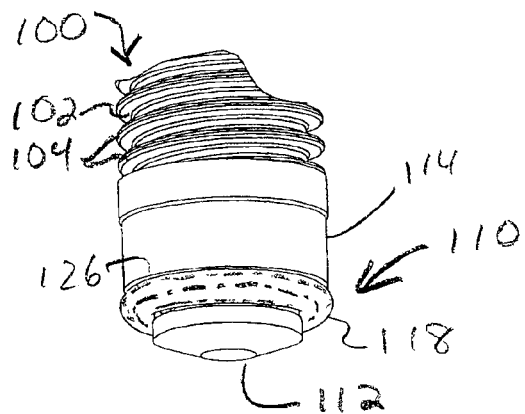
FIG. 4 is an enlarged view of the distal tip portion of the plunger of the syringe of FIGS. 1 and 2 containing the viscoselective seal of the present invention.

Connector 30 also is seen to have opposed wings 38 facilitating manual gripping thereof; and "finger grips" 28 extending laterally from container member 12 at proximal end 18, are seated within wings 38. Connector 30 may preferably comprise a pair of connector halves 30A, 30B that are securable to each other to secure therebetween adjacent portions of container member 12 and advancement mechanism 60 as may be discerned from FIG. 3; connector halves 30A, 30B may be identical to each other with cooperating joint-strengthening features defined along their adjoining edges 54.

Connector 30 is adapted to receive thereinto at proximal end 40 thereof, plunger 102 of actuator 100 and to be releasably affixable to actuator 100 by means of an advancement mechanism 60 disposed proximally of chamber 14. Advancement mechanism 60 is securable to connector 30 such as by a flange or lip 62 distally of a seat 82 cooperating with a corresponding flange or lip 42 proximally of a seat 52 within cylindrical body portion 34 of the connector to prevent movement in the axial direction while permitting rotational movement with respect thereto. Advancement mechanism 60 further includes an engagement section 64 for engaging actuator 100. Preferably, engagement section 64 comprises a pair of spaced apart legs 66 that coextend distally beyond flange 62 to free ends 68 disposed within cylindrical body portion 34 of connector 30. Each leg 66 includes an inwardly facing surface 70 that is threaded, and includes an outwardly directed surface 72 that is engageable with a cam section of the connector to deflect the legs radially inwardly upon cam engagement.

Advancement mechanism 60 is reciprocally rotatable with respect to connector 30 between first and second positions. Opposed projections 74 extend radially outwardly from short tubular body section 76 to facilitate relative manual rotation of the advancement mechanism with respect to connector 30. When in the first position, camming ribs 56 of connector 30 have deflected legs 66 radially inwardly about pivot sections 78 so that threaded surfaces 70 engage and mesh with corresponding threads 104 along opposed sides of plunger 102. When rotated into the second position, camming ribs 56 disengage from outer surfaces 72 of legs 66 to permit the legs to relax or resile outwardly thus disengaging the threaded surfaces 70 from threads 104 of plunger 102. When the advancement mechanism 60 is in the second position, plunger 102 is freely movable with respect to connector 30 and chamber 14; when the threaded surfaces of legs 66 are engaged with the threads of the plunger, only incremental axial movement is permitted by rotation of actuator 100.

Proximal end 40 of connector 30 is shown to include a circumferentially opposed pair of first detents 44 and first stops 46 that cooperate with respective ones of projections 74 to secure the advancement mechanism in the first position; similarly, a pair of second detents 48 and second stops 50 similarly cooperate with respective bearing surfaces 80 of projections 74 to secure the advancement mechanism in the second position. In FIG. 1, the advancement mechanism is in its first or unlocked position, with projections 74 engaged with the first detents 44 and first stops 46. An indicator 58 preferably is embossed on connector 30 to indicate the first or unlocked and second or locked positions and the direction of locking or unlocking. Also, preferably connector 30 is formed of translucent or transparent material to enable engagement with the threaded plunger, and the location of the plunger tip, to be visually verified.

Actuator 100 includes at its proximal end an actuating section 106 such as a handle that is manually grippable, with ears 108 extending laterally for mechanical advantage for manual rotation of the actuator with respect to the connector 30, when the advancement mechanism has been moved into its first position, for incremental advancement of the plunger along the chamber during an application procedure. Actuator 100 and especially plunger 102 may be made of polyacetal material especially when used to apply PMMA viscous material.

A viscoselective high pressure seal 110 of the present invention is defined at distal end portion 112 of plunger 102. A first embodiment of viscoselective seal 110 is illustrated in FIGS. 4 to 7. A distal tip member 114 includes a groove or seal seat 116 within which is seated a seal member 118. Distal tip member 114 is adapted to be affixed to the distal end 120 of plunger 102, and can include a boss 122 that is secured such as by force-fit within a passageway 124 of the plunger, as seen in FIG. 2. A collar 126 of distal tip member is just proximal of seal seat 116 to support seal member 118, which preferably is an O-ring such as of polytetrafluoroethylene (PTFE). Seal member 118 has an outer diameter just larger than the inner diameter of chamber 14, assuring compression of the outermost surface portions of the seal member against the sidewall inside surface of the chamber as it is moved axially therealong by plunger 102 during an application procedure, thus sealing the chamber.

Figure 5:
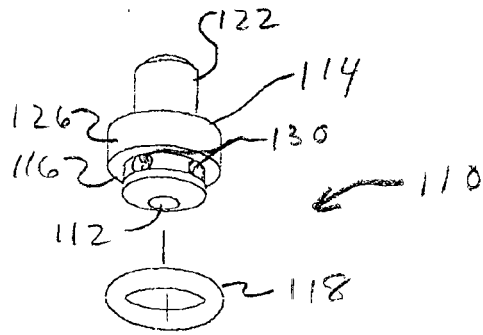
FIGS. 5 to 7 are exploded, elevation and cross-sectional views of the viscoselective seal of FIG. 4, with FIG. 7 taken along lines 7—7 of FIG. 6.
Figure 6:
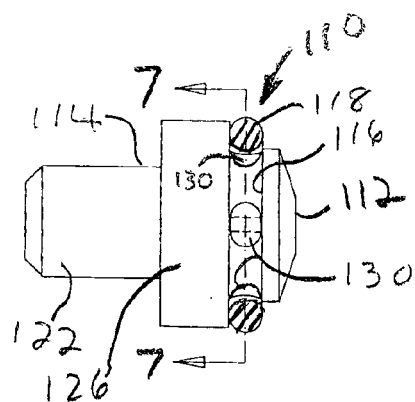
Figure 7:
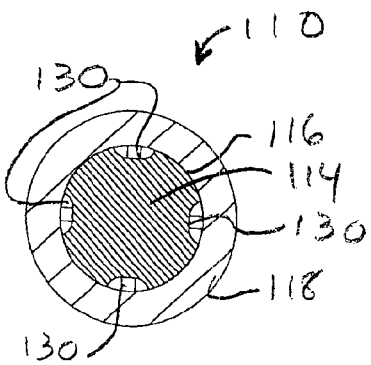

Seen in FIGS. 5 to 7 are a plurality of dimples 130 formed into the bottom surface of seal seat 116 spaced around the circumference. Seal member 118 is preferably slightly loosely seated in seat 116 upon assembly, such that dimples 130 define escape paths or vents for aspiration of air when plunger 102 is initially inserted into the entrance of chamber 14, with advancement mechanism 60 disengaged or unlocked. Upon abutment of plunger distal tip 112 against the proximal surface of the viscous material within chamber 14, most of the air has been easily and quickly aspirated past the seal member simply by urging the plunger into the connector and then the chamber, and the seal member is then pressed by the viscous material proximally against collar 126 of the distal tip member thus closing off any fluid escape path previously defined by the vents. Upon rotation of the advancement mechanism to its engaged or locked position, the seal member is assuredly pressed against collar 126 and prevents passage therepast of any viscous material as actuator is then rotated to move the plunger distal tip incrementally axially along the chamber to generate high pressure therewithin and express the viscous material from the chamber's distal tip 16 and into a tube or cannula to be conveyed to the treatment site for depositing the material. Distal tip member 114 may be made for example of plastic or of stainless steel. Optionally, grooves could be utilized instead of dimples; the grooves could have rounded or V-shaped bottom surfaces, and preferably extend axially. When the present invention is to be used with PMMA, the dimples (or grooves) could be about from 0.04 to 0.15 inches wide, such as about 0.078 inches, and about 0.04 inches deep and about 0.08 to 0.15 inches long, such as about 0.133 inches, to define satisfactory air passage vents that do not permit passage of PMMA. For use of the viscoselective seal of the present invention with other fluid materials of different viscosity, the actual dimensions of the dimples or grooves (or other vent designs) could vary for improved viscoselective performance.

Figure 8:
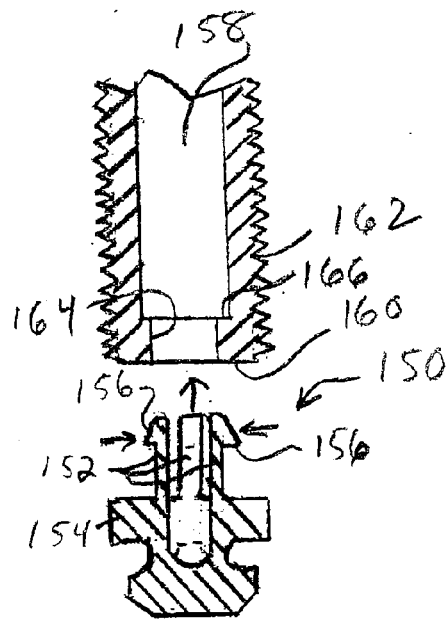
FIGS. 8 and 9 illustrate in cross-section another embodiment of distal tip member being secured to the plunger.
Figure 9:
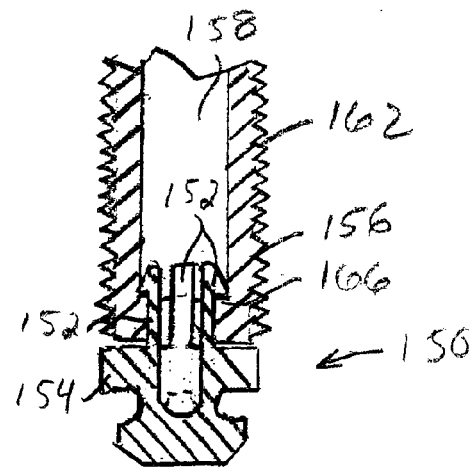

An alternate embodiment of distal tip member 150 is illustrated in FIGS. 8 and 9. Member 150 may include a plurality of arcuate latching legs 152 that extend proximally of collar 154, with latching members 156 at free ends of legs 152 extending radially outwardly. During insertion of legs 152 into bore 158 at distal end 160 of plunger 162, the legs are deflected radially inwardly past constriction 164 along to latch behind an internal shoulder 166 of bore 158. Such a distal tip member 150 may be molded for example of plastic material. Adhesive material or ultrasonic bonding may also be utilized to enhance the bond between the distal tip member and the plunger shaft.

Figure 10:
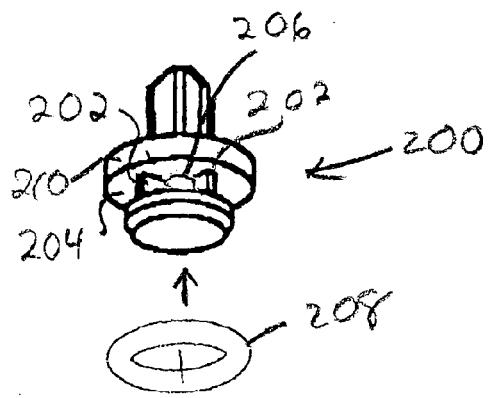
FIGS. 10 and 11 are isometric and cross-section views of a second embodiment of viscoselective seal.
Figure 11:
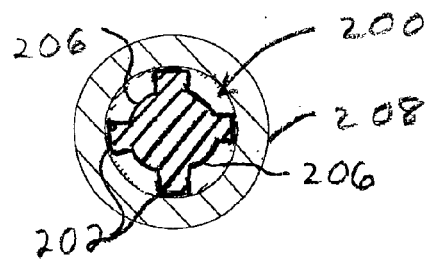

A second embodiment of viscoselective seal is shown in FIGS. 10 and 11. Distal tip member 200 includes a plurality of axially extending ribs 202 at seal seat 204. Vent regions 206 are defined between ribs 202 for escape of air until seal member 208 is pressed against collar 210.

Figure 12:
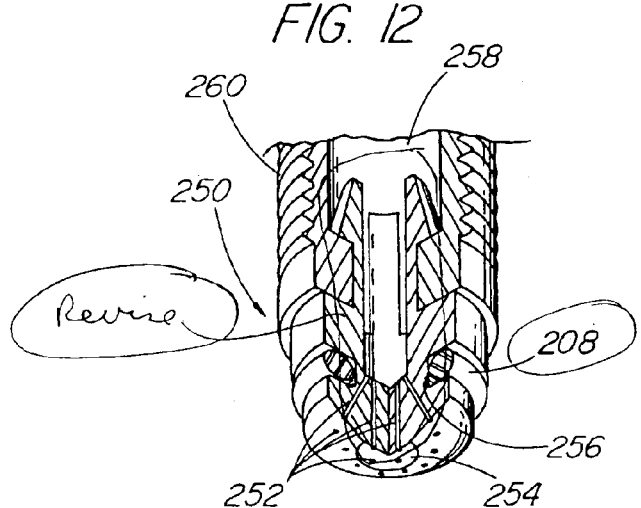
FIG. 12 illustrates a third embodiment of viscoselective seal wherein the distal tip member includes internal air escape vents.

A third embodiment of viscoselective seal is shown in FIG. 12. Distal tip member 250 is shown to include one or more very small dimensioned apertures 252 extending proximally from distal tip 254 to exit proximally of seal seat 256 such as into a bore 258 of the plunger shaft 260 which includes other apertures (not shown) communicating with the exterior surface of the actuator near the proximal end. The size of apertures 252 is selected such that viscous material for which the syringe is intended would not enter the apertures even under high pressure. The distal tip member is similar to member 150 of FIGS. 8 and 9 and may be molded of plastic material. The very small apertures could be formed, for example, by laser and be about 0.01 to 0.25 inches wide, when used with PMMA; for other materials of differing viscosity, other dimensions may yield improved performance.

Figure 13:
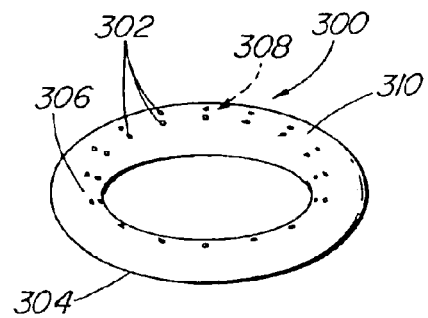
FIGS. 13 and 14 illustrate fourth and fifth embodiments of viscoselective seals in which the seal member provides air escape vents.
Figure 14:
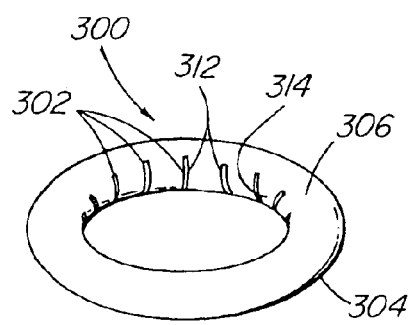

Fourth and fifth embodiments of viscoselective seals are shown in FIGS. 13 and 14. Seal member 300 is shown to include very small vents 302 that extend from distal surface 304 to proximal surface 306. Small vents 302 may be, for example, apertures 308 through the body 310 of the seal member (FIG. 13), or may be grooves 312 along the radially inwardly facing surface 314 (FIG. 14). The vents 302 may also be dimensioned to be sufficiently small that the viscous material cannot enter, or may become essentially or completely closed when the seal member is compressed upon being pressed against the collar of the distal tip member by initial engagement with the viscous material during an application procedure, thus permitting the vents to be larger. The apertures or grooves could be formed by laser.

Figure 15:
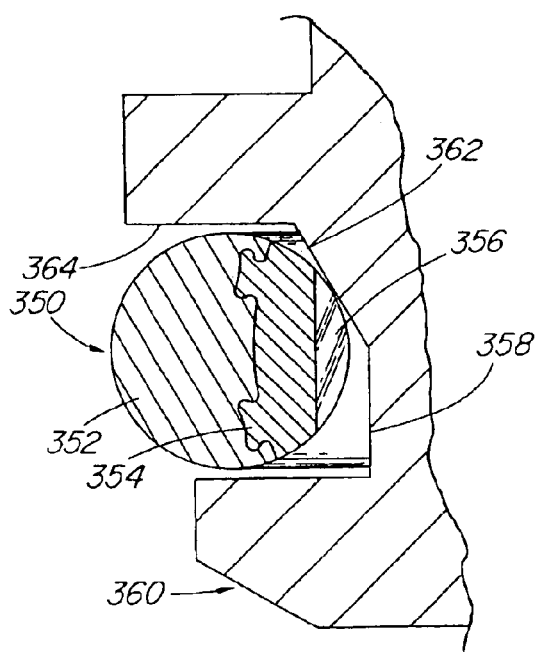
FIG. 15 illustrates a sixth embodiment of viscoselective seal in an enlarged part cross-section view.

A sixth embodiment, similar to the viscoselective seal of FIGS. 13 and 14, is illustrated in FIG. 15 and includes a seal member 350 that may comprise an essentially incompressible radially outward portion 352 such as of PTFE, and a somewhat more compressible radially inward portion 354 such as of silicone rubber bonded thereto that contains vents such as grooves 356 similar to grooves 314 of FIG. 14. The seal seat 358 of the distal tip member 360 may include a tapered proximal portion 362 to its proximal end wall 364 to facilitate compression of the radially inward portion of the seal member as the seal member is pressed against the proximal end wall.

Prevention of the escape of the viscous material past the seal at the distal tip of the plunger is desirable to attain sufficiently complete fluid material containment to enable achievement of the desired high pressure, but a certain minimal level of fluid passage could still permit assured achievement of the high pressure desired; materials such as bone cement that escape past the plunger tip can quickly inhibit or even lock up movement of the plunger during an application procedure, possibly causing serious complications and at least lengthening the procedure.

The present invention permits easy and quick aspiration of air from the chamber when the actuator is moved into position, without delay or special procedures. For example, with some conventional syringes, the chamber must be held inverted for a length of time after the plunger is initially inserted to permit air to rise through the viscous material to escape from the open small diameter distal end of the chamber; complete aspiration of air is critical in such a medical procedure as vertebroplasty. The provision of the advancement mechanism with locked and unlocked positions permits quick initial connection of the actuator with the container, as well as the eventual desired incremental plunger advancement needed to manually generate the high pressures required.

Pressures of from 1000 psi to 2000 psi or even higher, are expected with the high pressure injection syringe of the present invention through simple manual operation. Such high pressure levels may enable the viscosity of the fluid material to be increased above that level presently seen in medical procedures. Such higher viscosity in PMMA bone cement is medically advantageous, in that the higher viscosity assures that the bone cement remains precisely where it has been injected and does not seep or travel to unintended or undesirable collateral locations prior to curing.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit of the invention and the scope of the claims.

What is claimed is:

1. A syringe comprising:
a chamber for receiving a plunger of an actuator, the plunger being movable axially with respect to the chamber when the actuator is operated;
a connector to be fixed relative to the chamber and to facilitate entry of the plunger into the chamber, and
a viscoselective high pressure seal associated with the plunger, wherein the plunger comprises a distal tip portion adapted to define the viscoselective high pressure seal, the distal tip portion comprising a seal member therearound so sized for its radially outwardly directed surface to assuredly sealingly engage an inside surface of the chamber during an application procedure but movable therealong during actuation of the plunger, and at least one relatively small aperture extends longitudinally within the plunger tip portion from distally of the seal member to proximally thereof, passing under the seal member, the aperture being sufficiently small to effectively inhibit passage of viscous material therealong and define an air escape vent.

2. The syringe of claim 1, wherein the seal member is an O-ring of material having a limited resilience.

3. The syringe of claim 1, wherein the plunger distal tip portion comprises a circumferential seal seat just proximally of a distal end thereof in which is disposed the seal member.

4. The syringe of claim 3, wherein the seal seat has a geometry that provides for escape of air between the seal member and the seat bottom surface.

5. The syringe of claim 3, wherein the seal seat permits slight axial movement of the seal member within the seal seat.

6. The syringe of claim 3, wherein small vents extend longitudinally from distally of the seal member to proximally thereof prior to the seal member being urged to a most proximal position by viscous material during actuation of the plunger.

7. The syringe of claim 1,
wherein the connector includes an advancement mechanism adapted to be moved between first and second positions to engage with and disengage from the actuator for providing for both incremental advancement of the plunger in the chamber, and free axial movement thereof, respectively.

8. The syringe of claim 7, wherein the advancement mechanism has threaded surfaces to cooperate with corresponding threaded surfaces on the plunger when engaged, so that the plunger is constrained to move longitudinally only incrementally with respect to the connector and the chamber as the actuation section is rotated.

9. The syringe of claim 8, wherein the connector is rotatable between first and second positions and the threaded surfaces are defined on deflectable sections where, in the first position, the threaded sections have been deflected radially inwardly by a cam of the connector to engage the plunger threads, and where, in the second position, the threaded sections have disengaged from the cam and resile radially outwardly to be disengaged from the plunger allowing the plunger to be movable freely longitudinally.

10. A syringe comprising:
a chamber extending to a distal tip portion and having a proximal end adapted to receive thereinto an actuator that is movable axially with respect to the chamber;
an actuator having a plunger extending to a distal tip portion associated with the chamber distal tip portion, and further having an actuation section at a proximal end of the plunger, wherein the distal tip portion of the plunger is adapted to define a viscoselective high pressure seal with respect to the chamber distal dip portion; and
a connection affixable to the chamber for enabling connection of the actuator to the chamber, wherein the plunger distal tip portion comprises a seal member therearound so sized for its radially outwardly directed surface to assuredly sealingly engage an inside surface of the chamber during an application procedure but be movable therealong during actuation of the plunger, and wherein at least one very small aperture extends longitudinally within the plunger tip portion from distally of the seal member to proximally thereof, passing under the seal member, the aperture being sufficiently small to effectively inhibit passage of viscous material.

11. A syringe comprising:

a chamber extending to a distal tip portion and having a proximal end adapted to receive thereinto an actuator that is movable axially with respect to the chamber;

an actuator having a plunger extending to a distal tip portion associated with the chamber distal tip portion, and further having an actuation section at a proximal a end of the plunger, wherein the distal tip portion of the plunger is adapted to define a viscoselective high pressure seal with respect to the chamber distal dip portion; and a connector affixable to the chamber for enabling connection of the actuator to the chamber, wherein the plunger distal tip portion comprises a seal member therearound so sized for its radially outwardly directed surface to assuredly sealingly engage an inside surface of the chamber during an application procedure but be movable therealong during actuation of the plunger, wherein the plunger distal tip portion comprises a circumferential seal seat just proximally of a distal end thereof in which is disposed the seal member, and wherein the seal seat has geometry that provides for escape of air between the seal member and seat bottom surface.

12. A syringe comprising:

a chamber extending to a distal tip portion and having a proximal end adapted to receive thereinto an actuator that is movable axially with respect to the chamber;

an actuator having a plunger extending to a distal tip portion associated with the chamber distal tip portion, and further having an actuation section at a proximal end of the plunger, wherein the distal tip portion of the plunger is adapted to define a viscoselective high pressure seal with respect to the chamber distal dip portion; and a connector affixable to the chamber for enabling connection of the actuator to the chamber, wherein the plunger distal tip portion comprises a seal member therearound so sized for its radially outwardly directed surface to assuredly sealingly engage an inside surface of the chamber during an application procedure but be movable therealong during actuation of the plunger, wherein the plunger distal tip portion comprises a circumferential seal seat just proximally of a distal end thereof in which is disposed the seal member, and wherein the seal seat permits slight axial movement of the seal member within the seal seat and wherein small vents extend longitudinally from distally of the seal member to proximally thereof prior to the seal member being urged to a most proximal position by viscous material during actuation of the plunger.

* * * * *